Figure 1:
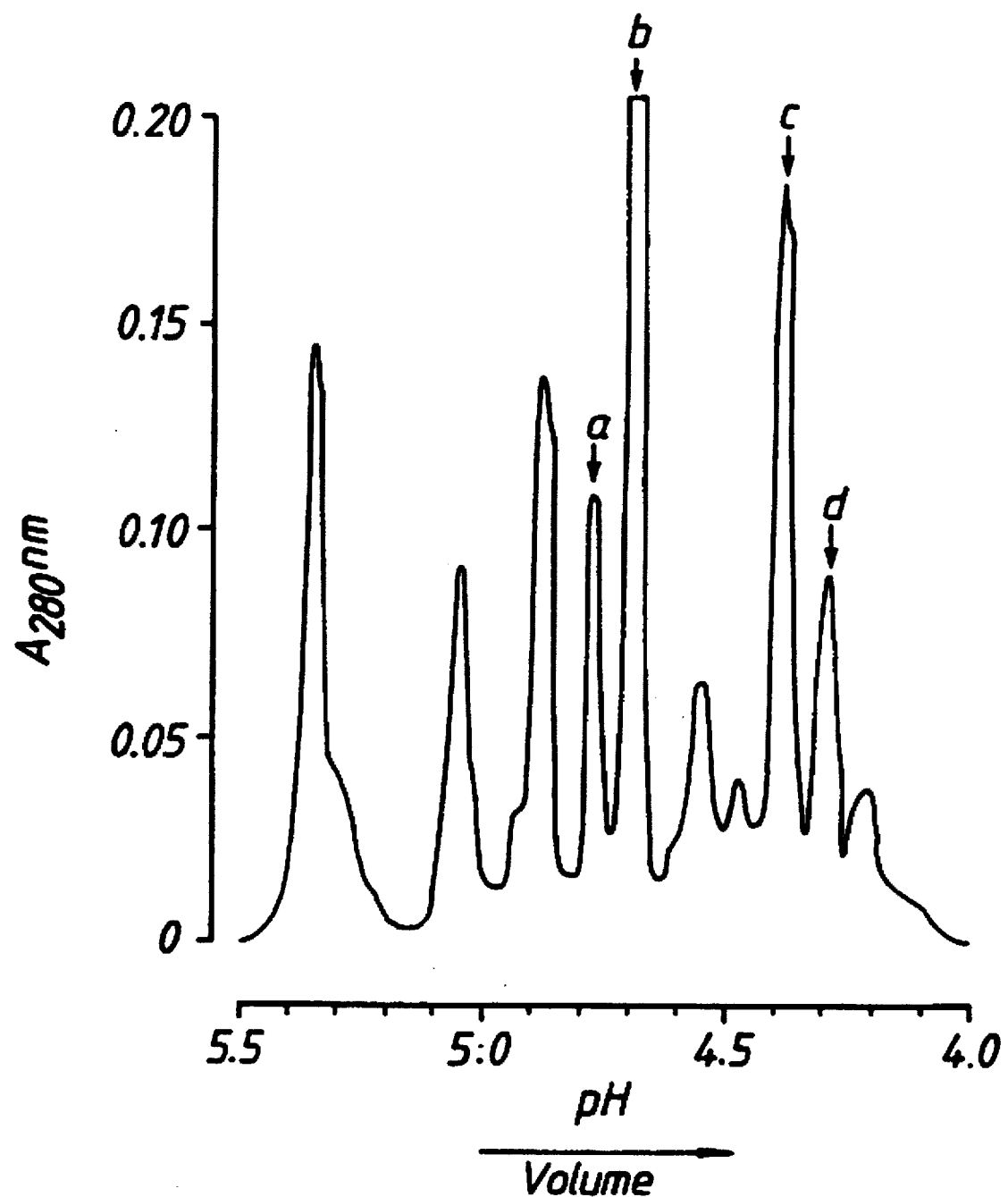
Figures 2A, 2B:
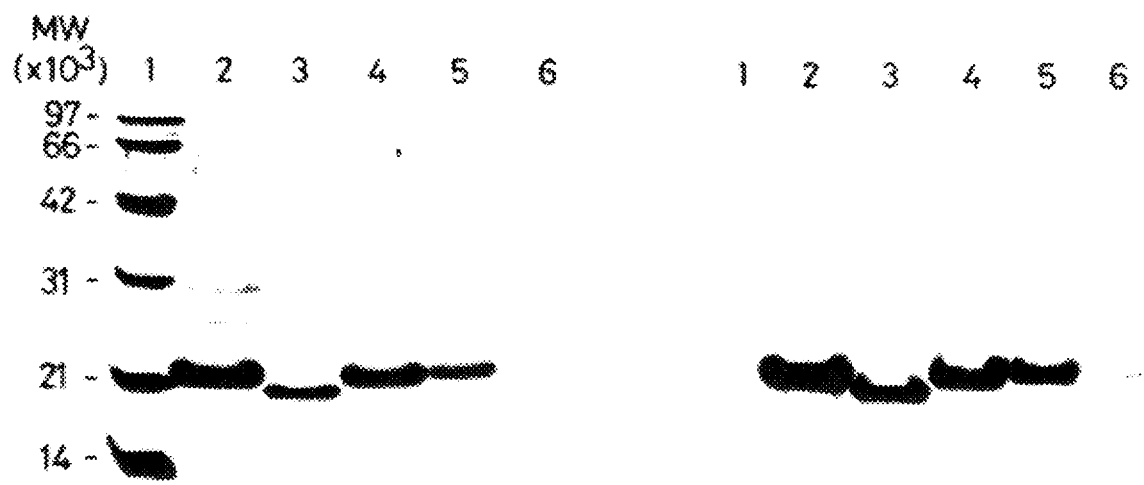

United States Patent [19]
Wood et al.

[11] Patent Number: 5,693,500
[45] Date of Patent: Dec. 2, 1997

[54] **DIAGNOSIS OF *MYCOBACTERIUM BOVIS* INFECTION**

[75] Inventors: Paul Richard Wood, Lower Templestowe; Anthony John Radford, Kew; Theodora Fifis, North Balwyn, all of Australia

[73] Assignee: Commonwealth Scientific and Industrial Research Organisation, Australia

[21] Appl. No.: 453,750

[22] Filed: May 30, 1995

Related U.S. Application Data

[62] Division of Ser. No. 104,927, Aug. 12, 1993, which is a continuation of Ser. No. 585,094, Oct. 17, 1990, abandoned.

[30] Foreign Application Priority Data

Mar. 31, 1988 [AU] Australia .................... PI7550/88

[51] Int. Cl.⁶ .................... C12N 15/31; C07K 14/35; C07H 21/04; C12Q 1/68
[52] U.S. Cl. .................... 435/69.3; 435/6; 435/252.33; 435/320.1; 530/395; 530/820; 536/23.7
[58] Field of Search .................... 530/395, 820; 435/6, 69.3, 252.33, 320.1; 536/23.7

[56] References Cited

U.S. PATENT DOCUMENTS 4,358,535  11/1982  Falkow et al. .................... 435/5

FOREIGN PATENT DOCUMENTS 8700061   7/1987   WIPO.
87/05400  9/1987   WIPO.

OTHER PUBLICATIONS

Mehra et al., "Efficient Mapping of Protein Antigenic Determinants," Proc. Natl. Acad. Sci 83:7013–7017 (1986).

Young et al., "Dissection of *Mycobacterium tuberculosis* Antigens Using Recombinant DNA," Proc. Natl. Acad. Sci 82:2583–87 (1985).

"Serological reactivity to *Mycobacterium bovis* protein antigens in cattle"; Fifis et al.; *Veterinary Microbiology*, 30(1992); pp. 343–354.

"The Tuberculin Skin Test"; Snider, Jr.; *American Review of Respiratory Disease*; 1982; p. 108 only.

"Diagnostic Skin Test for Mycobacterial Infections in Man"; Hsu; *Chest*; 1973; p. 1 only.

"The Tuberculin Skin Test"; Cornstock et al.; *American Review of Respiratory Disease*; 1971; p. 769 only.

"Comparative Studies with Various Substrains of *Mycobacterium bovis* BCG on the Production of an Antigenic Protein, MPB70", Miura et al., *Infection and Immunity*; 1983; pp. 540–545.

"Subdivision of Daughter Strains of Bacille Calmette–Guerin (BCG) According to Secreted Protein Patterns"; Abou–Zeid et al.; *Journal of General Microbiology*; vol. 132; p. 3047 (1986).

"The Secreted Antigens of *Mycobacterium tuberculosis* and Their Relationship to Those Recognized by the Available Antibodies"; Abou–Zeid et al.; *Journal of General Microbiology*; 1988; p. 531 only.

"The sensitivity and specifity of various tuberculin tests using bovine PPD and other tuberculins"; Francis et al.; *The Veterinary Record*; vol. 103, Nov. 4, p. 420 (1978).

"Sensitization of cattle to bovine and avian tuberculins with *Mycobacterium cookii*"; Monaghan; *The Veterinary Record*; 1991; p. 383 only.

"The comparative tuberculin test in guinea pigs using PPD extracts prepared from mycobacteria killed with phenol"; Choi et al.; *Autralian Veterinary Journal*; 1982; p. 183 only.

"New Tuberculins"; *The Lancet*; 1984; p. 199 only.

"Mycobacterial Antigens"; *The Lancet*; 1984; p. 199 only.

"Mycobacterial Antigens: a Review of Their Isolation, Chemistry, and Immunological Properties"; Daniel et al.; *Microbiological Review*; 1978; p. 84 only.

"Mapping of the T and B cell epitopes of the *Mycobacterium bovis* protein, MPB70"; *Immunol. Cell Biol.*; 1990; pp. 359–365.

"Epitope mapping of the *Mycobacterium bovis* secretory protein MPB70 using overlapping peptide analysis"; Radford et al.; *Journal of General Microbiology*; 1990; p. 265–272.

"Humoral Immune Response in Human Tuberculosis: Immunoglobulins G, A, and M Directed against the Purified P32 Protein Antigen of *Mycobacterium bovis* Bacillus Calmette–Guerin", Turneer et al.; *Journal of Clinical Microbiology*; 1988; pp. 1714–1719.

"The Use of Murine Monoclonal antibodies without Purification of Antigen in the Serodiagnosis of Tuberculosis"; Hewitt et al.; *Journal of Immunological Methods*; 1982; pp. 205–211.

"Evaluation of a monoclonal antibody (TB72) based serological test for tuberculosis"; Ivanyi et al.; *Clin. exp. Immunol.*; 1983; pages 337–345.

"Control by H–2 genes of murine antibody responses to protein antigens of *Mycobacterium tuberculosis*"; Ivanyi et al.; *Immunology*; 1986; pp. 329–332.

"The Serodiagnosis of Tuberculosis and other Mycobacterial Diseases by Enzyme–linked Immunosorbent Assay"; Daniel et al.; *American Review of Respiratory Disease*; 1987; pp. 1137–1151.

(List continued on next page.)

*Primary Examiner*—Michael P. Woodward
*Attorney, Agent, or Firm*—Bacon & Thomas

[57] ABSTRACT

A method for the diagnosis of *Mycobacterium bovis* infection in a susceptible animal, comprises detection in said animal of antibodies against the MPB-70 protein of *M. bovis* and/or the detection of a cell-mediated immune response of said animal to the said MPB-70 protein. Also disclosed is a recombinant DNA molecule corresponding to all or portion of the *M. bovis* DNA sequence coding for the MPB-70 protein or a polypeptide having the antigenicity of MPB-70 protein, or degenerate forms thereof, as well as recombinant MPB-70 protein or polypeptide and a process for the preparation thereof.

12 Claims, 3 Drawing Sheets

OTHER PUBLICATIONS

"Improvements in the Diagnosis of Tuberculosis"; Bates et al.; *Future Research in TB;* pp. 415–417.

"The Rapid Diagnosis of Paucibacillary Tuberculosis"; *Tubercle;* 1989; pp. 1–4.

"Complete Nucleotide Sequence of Immunogenic Protein MPB70 from *Mycobacterium bovis* BCG"; Terasaka et al.; *FMES Microbiology Letters,* 58:273–276 (1989).

"Purification of a Major *Mycobacterium bovis* Antigen for the Diagnosis of Bovine Tuberculosis"; Fifis et al.; *Scand. J. Immunol.;* 29, 91–101 (1989).

"Genetic Influences on the Immune Repertoire Following Tuberculosis Infection in Mice"; Brett et al.; *Immunology;* 71:113–119 (1990).

"Accessment of an enzyme linked immunosorbent assay for the detection of cattle infected with *Mycobacterium bovis*"; L.A. Auer, *Australian Veterinary Journal;* vol. 64, No.6; Jun. 1987.

Nagai et al.; *Infection and Immunity;* 31:1152–1160 (1981).

"Protein Purification"; Scopes, R.K.; (Springer–Verlag, NY) pp. 85–88 (1982).

Harboe et al.; *Infection and Immunity;* 52:293–302 (1986).

Vaccines 86: new approaches to immunization, pp. 219–224; M.E. Patarroyo et al.; "Immunogenic Synthetic Peptides Against *Mycobacterium tuberculosis*"; Cold Spring Harbor Laboratory, 1986.

*Infection and Immunity;* vol. 56, No. 4; pp. 921–925; A.J. Radford et al.; "Cloning of a Species–Specific Antigen of *Mycobacterium bovis*"; 1988.

*Journal of General Microbiology;* vol. 134, No. 9, pp. 2599–2604; P.R. Wood et al.; "Production and Characterization of Monoclonal Antibodies Specific for *Mycobacterium bovis*"; 1988.

*Scandinavian Journal of Immunology;* vol. 25, No. 4, pp. 445–454; K. Haslov et al.; "Biological Activity in Sensitized Guinea Pigs of MPB–70, a Protein Specific for some strains of *Mycobacterium bovis* BCG"; 1987.

*Infection and Immunity;* vol. 55, No. 12, pp. 3213–3214; C. Abou–Zeid et al.; "Characterization of the Secreted Antigens of *Mycobacterium bovis* BCG: comparison of the 46 KD Dimeric Protein with Protein MPB–64 and MPB–70"; 1987.

*American Review of Respiratory Diseases;* vol. 129, pp. 444–452; M. Harboe et al.; "MPB–70, A Unique Antigen of *Mycobacterium bovis* BCG"; 1984.

MPB70 DNA AND INFERRED AMINO ACID SEQUENCE

```
1    G  D  L  V  G  P  G  C  A  E  Y  A  A  A  N  P  T  G  P  A
1    GGCGATCTGGTGGGCCCGGGCTGCGCGGAATACGCGGCAGCCAATCCCACTGGGCCGGCC

21   S  V  Q  G  M  S  Q  D  P  V  A  V  A  A  S  N  P  E  L
61   TCGGTGCAGGGAATGTCGCAGGACCCGGTCGCGGTGGCCGCTCGAACAATCCGGAGTTG

41   T  L  T  A  A  L  S  G  L  N  P  Q  V  N  L  V  D  T
121  ACAACGCTGACGGCTGCACTGTCGGGCCTCAATCCGCAAGTAAACCTGGTGGACACC

61   L  N  S  G  Q  Y  T  V  F  A  R  T  N  A  A  F  S  K  L  P
181  CTCAACAGCGGTCAGTACACGGTGTTCGCACGGACCAACGCGGCATTTAGCAAGCTGCCG

81   A  S  T  I  D  E  L  K  T  N  S  S  L  T  S  I  L  T  Y
241  GCATCCACGATCGACGAGCTCAAGACCAATTCGTCACTGACCAGCATCCTGACCTAC

101  H  V  A  G  Q  T  S  P  A  N  V  G  T  R  Q  T  L  Q
301  CACGTAGTGGCCAAACAGTCCCGGCCAACGTCGGCACCCGTCAGACCCTCCAG

121  G  A  S  V  T  V  T  G  Q  G  N  S  L  K  V  G  N  A  D  V
361  GGCGCCAGCGTGACGGTGACGGGTCAGGGTAACAGCTTCAAGGTCGGTAACGCCGACGTC

141  V  C  G  G  V  S  T  A  N  A  T  V  Y  M  I  D  S  V  L  M
421  GTCTGTGGGGGTGTCTACCGCCAACGCGACGGTGTACATGATTGACAGCGTGCTAATG

161  P  P  A  *
481  CCTCCGGGCGTAA
```

Fig. 3.

DIAGNOSIS OF *MYCOBACTERIUM BOVIS* INFECTION

This application is a division of Ser. No. 08/104,927, filed Aug. 12, 1993; which is a continuation of Ser. No. 07/585,094, filed Oct. 17, 1990 (abandoned).

This invention relates to the diagnosis of bovine tuberculosis, and in particular it relates to the use of a particular species-specific antigen for the diagnosis of *Mycobacterium bovis* infection, such as bovine tuberculosis, by both antibody and cellular assays.

Bovine tuberculosis (BTB) is a major disease of cattle worldwide. In the Americas alone it was estimated to have cost the cattle industry $83 million in 1977 (World Health Organisation, 1983). Several nations have mounted or are running campaigns to eliminate BTB, and although these campaigns have drastically reduced the incidence of the disease, none have been totally successful. In many parts of the world there is no concerted effort to control the disease, which poses human, as well as animal, health risks. The causative agent of bovine tuberculosis, *Mycobacterium bovis*, is closely related to *M. tuberculosis*.

Eradication of the disease from cattle has been hampered by the lack of sensitivity and specificity of the bovine skin test currently used for detection of infected animals. A simple serological test for BTB would be the preferred option, but there are two fundamental problems with any test for *M. bovis*-specific antibody. Infected animals generally have low levels of antibody to *M. bovis*, and many of the antibodies produced cross-react with antigens from other environmental mycobacterial or nocardial species (Daniel et.al., 1978). Enzyme-linked immunoassays using *M. bovis* protein extracts as antigens have been used to detect infected cattle (Ritacco et.al., 1987; Theon et.al., 1983), but these tests using crude antigens appear to lack sufficient specificity or sensitivity to be acceptable for use in an eradication campaign (Auer, 1987). These problems are common to the serological diagnosis of all mycobacterial infections.

The MPB-70 protein is a major antigen of *Mycobacterium bovis* and *M. bovis*/BCG strains and can constitute more than 10% of the total protein present in culture filtrate preparations from these organisms. (Nagai et.al., 1981; Harboe and Nagai, 1984). It has been shown that this protein induces a potent delayed skin test reaction in *M. bovis*/BCG immunized guinea pigs and has limited cross-reactivity with other species of Mycobacteria, (Harboe et.al., 1986; Haslov, et.al., 1987).

In work leading to the present invention, the utility of this antigen in antibody and cellular assays for the diagnosis of *M. bovis* infections in cattle has been examined. The MPB-70 protein was found to be expressed by all bovine field isolates of *M. bovis* tested (151 separate field isolates, Table 1) and was not present in various other mycobacteria commonly found in the environment.

Accordingly, the present invention provides a method for the diagnosis of *Mycobacterium bovis* infection in susceptible animal, which is characterised by the detection in said animal of antibodies against the MPB-70 protein of *M. bovis* and/or the detection of a cell-mediated immune response of said animal to the said MPB-70 protein.

In essence, the present invention is based on the use of the MPB-70 protein as a specific antigen for the diagnosis of *M. bovis* infection. MPB-70 may be used as an antigen in a test for antibody to *M. bovis* in accordance with any of the commonly known antibody tests, such as ELISA, RIA, CFT methods, and the like. MPB-70 may also be used as an antigen in the caudal fold skin test in vivo, as well as an antigen in in vitro assays for cell-mediated immune responses such as proliferation assays or assays based on the release of gamma interferon or interleukin 2.

Whilst the present invention is particularly directed to the diagnosis of *M. bovis* infection in cattle, causing bovine tuberculosis, the method of the invention extends to detection of *M. bovis* infection in any other susceptible animal species, including for example, deer, badgers, possums, pigs and camels.

The present invention also extends to a process for the purification of MPB-70 from *M. bovis* culture filtrate material, as well as to the production of recombinant MPB-70 by cloning and expression in a host cell such as *E. coli*.

It will of course be appreciated that the references to MPB-70 protein herein include not only the full protein, but also any polypeptides derived therefrom which have the antigenicity of MPB-70 and therefore can be used in the assays described herein in the same manner as MPB-70 protein itself.

The MPB-70 protein has been purified from an *M. bovis* culture filtrate by chromatofocusing on a Mono-P column. FIG. 1 shows a typical elution profile with the arrowed peaks containing the majority of the MPB-70 antigen. When the fractions in each peak were pooled and probed on Western blots with a monoclonal antibody specific for MPB-70, a protein of 22 kd molecular weight was detected (FIG. 2).

Purified MPB-70 has been examined using both in vivo and in vitro cellular assays. The in vivo tests were carried out using the conventional skin test in both guinea pigs sensitized with killed *M. bovis* cells and cattle infected with live *M. bovis*. MPB-70 induced a positive reaction in both immunised guinea pigs (Table 2) and infected cattle (Table 3) although not as strong as that induced by bovine tuberculin Purified Protein Derivative (PPD) at similar concentrations. MPB-70 has also been tested in vitro for the ability to stimulate proliferation of peripheral blood lymphocytes from *M. bovis* infected cattle. The level of reactivity to MPB-70 was similar in all the *M. bovis* infected animals and there was no activity with lymphocytes from uninfected control cattle (Table 4).

In order to ascertain its suitability as a specific antigen for detection of *M. bovis* infected cattle, MPD-70 has been tested in an antibody assay (ELISA). Crude culture filtrate antigen was used for comparison in the antibody assay and the antibody results were compared with the conventional in vivo caudal fold skin test. Although the sensitivity of the MPB-70 ELISA was less than that achieved with both the crude antigen ELISA and the caudal fold test, the specificity of this assay was far superior with only a few false positive results (Table 5). The low sensitivity of the antibody assay was most likely due to the fact that mycobacteria preferentially induce a T cell rather than a humoral response (Thorns and Morris, 1983).

In further investigations, the MPB-70 gene from *M. bovis* has been cloned into the λgtll expression vector and its DNA sequence determined. The sequence of MPB-70 so determined differs considerably from that deduced by Patarroyo et.al., (1986;1986a) using protein sequencing methods (FIG. 3). When serum samples from *M. bovis* infected cattle were screened by Western blotting on a variety of recombinant *M. bovis* fusion proteins, MPB-70 was shown to be the dominant antigen recognised (Table 6). The recombinant MPB-70 protein has also been found to induce good cellular responses in *M. bovis* immunized guinea pigs and cattle.

Determination of the DNA sequence of the MPB-70 gene enables production of DNA probes corresponding to all or a portion of this DNA sequence, and the use of such a probe for the detection of *M. bovis* or *M. bovis*/BCG organisms in samples such as cultures, sputum or tissue samples. Accordingly, in another aspect of this invention there is provided a method for the detection of *M. bovis* or *M. bovis*/BCG organisms in a sample, which comprises the steps of contacting said sample with a DNA probe corresponding to all or a portion of the DNA sequence of the MPB-70 gene, and detecting binding of said probe to indicate the presence of said organisms in said sample.

TABLE 1

Immunoperoxidase Staining of *Mycobacterius bovis* and other bacteria with a monoclonal antibody specific for MPB-70

| Positive | Negative |
|---|---|
| *M. bovis* strain TMC[1] 410 | *M. africanum* strain TMC 5122 |
| *M. bovis* strain AN5 | *M. microti* strain TMC 601 |
| *M. bovis* strain PMC[2] 203 | BCG[3] strain Glaxo |
| *M. bovis* strain PMC 205 | BCG strain Copenhagen |
| *M. bovis* strain PMC 259 | *M. tuberculosis* strain H37Rv |
| *M. bovis* field strains - CSIRO 50 | (CSIRO daughter strain) |
| - S.A.[5] 78 | M.A.I.S.[4] serovars 2, 6, 8, 9, 10, 15, 18 |
| - Vic.[6] 16 | *M. gordonae* |
| - Qld.[7] 2 | *M. phlei* |
| - N.Z.[8] 5 | *M. kansasii* |
| BCG strain Moreau | *M. paratuberculosis* |
| BCG strain Tokyo | *M. flavescens* |
| BCG strain Pasteur | *Nocardia asteroides* |
| BCG strain CSL[9] | *Brucella melitensis* strain 16M |
| *M. tuberculosis* strain H37Rv | *B. abortus* strain 19 |
| (Qld daughter strain) | *Rhodococcus equi* |
| *M. tuberculosis* strain DT | *R. rhodochrous* |
| *M. tuberculosis* strain C | |
| *M. tuberculosis* strain PN | |
| *M. tuberculosis* field strains - 7 | |

[1]TMC = Trudeau Mycobacteria Collection
[2]PMC = Parkville Mycobacteria Collection
[3]BCG = Bacille Calmette-Guerin
[4]M.A.I.S. = *Mycobacterium avium-intracellulare-scrofulaceum* complex
[5]S.A. = South Australia
[6]Vic = Victoria
[7]Qld = Queensland
[8]N.Z. = New Zealand
[9]CSL = Commonwealth Serum Laboratories

TABLE 2

Delayed skin response to bovine PPD[1] and to purified MPB-70 in guinea pigs sensitized with killed *M. bovis* strain AN5[3].

| | | Response | |
|---|---|---|---|
| Antigen | Concentration ng/50 μl[2] | Diameter mm (mean ± S.D.) | Area mm² (mean ± S.D.) |
| Bovine PPD | 350.0 | 12.62 ± 1.51 | 169.0 ± 32.3 |
| | 35.0 | 9.80 ± 1.47 | 98.5 ± 29.6 |
| | 3.5 | 2.16 ± 3.49 | 14.8 ± 26.1 |
| MPB-70 | 350.0 | 12.2 ± 1.10 | 149.8 ± 27.7 |

TABLE 2-continued

Delayed skin response to bovine PPD[1] and to purified MPB-70 in guinea pigs sensitized with killed *M. bovis* strain AN5[3].

| | | Response | |
|---|---|---|---|
| Antigen | Concentration ng/50 μl[2] | Diameter mm (mean ± S.D.) | Area mm² (mean ± S.D.) |
| | 35.0 | 7.9 ± 0.89 | 65.4 ± 16.8 |
| | 3.5 | 0.0 | 0.0 |

[1]. concentration of PPD is based on known biological activity.
[2]. concentration of purified antigens is based on freeze-dried weight.
[3]. control animals did not show any response.

TABLE 3

Delayed skin response to bovine PPD and purified MPB-70 in cattle infected with live *M. bovis*.

| | | PPD | | MPB-70 | |
|---|---|---|---|---|---|
| Animal No. | *M. bovis*+ | Diam (mm) | Skin thickness (mm²) | Diam (mm) | Skin thickness (mm²) |
| 213 | I.V. | 40 | 14.7 | 35 | 9.6 |
| 221 | I.T. | 65 | 20.6 | 45 | 9.6 |
| 249 | I.T. | 40 | 7.1 | 11 | 16.0 |
| 250 | I.V | 40 | 14.1 | 35 | 9.2 |
| 253 | I.V. | 35 | 10.0 | 25 | 6.8 |
| 259 | I.T. | 10 | 14.5 | 40 | 10.1 |
| 230 | Nil | 0 | 0.1 | 0 | 0.1 |
| 265 | Nil | 0 | 4.3 | 0 | 1.2 |

Bovine PPD 0.1 mg, MPB-70 0.08 mg,
+10⁶ *M. bovis* injected either intravenously (I.V.) or intratrachealy (IT)

TABLE 4

Proliferative response of bovine lymphocytes from *M. bovis* infected cattle to bovine PPD and purified MPB 70.

| | | Antigen | |
|---|---|---|---|
| Animal | Immunization | PPD | MPB-70 |
| 81 | AN5 immunized | 11.8 | 9.1 |
| 219 | NIL | 1.0 | 1.0 |
| 230 | NIL | 1.5(1.1)# | 0.7(1.1) |
| 220 | i.t. +*M. bovis* | 16.1(23.0) | 5.7(8.7) |
| 252 | i.t. *M. bovis* | 10.2(37.3) | 2.9(5.2) |
| 275 | i.t. *M. bovis* | 28.8(60.4) | 4.7(9.5) |
| 269 | i.v. +*M. bovis* | 60.6(87.6) | 13.5(17.6) |
| 277 | i.v. *M. bovis* | 43.4(41.3) | 5.4(5.6) |

*M. bovis* PPD 20 μg/ml.
purified MPB-70 50 μg/ml.
Animals tested 8 weeks post infection.
Results reported as stimulation indexes two separate experiments.
+i.t. = intratracheal, i.v. = intravenous.

TABLE 5

Comparison of an antibody assay using MPB-70 or crude antigen with the caudal fold test.

| Test Results | Caudal fold Test | MPB-70 ELISA | Crude antigen ELISA | |
|---|---|---|---|---|
| True Positive | 85 | 40 | 68 | culture positive animals |
| False Negative | 11 | 56 | 28 | |

TABLE 5-continued

Comparison of an antibody assay using MPB-70 or crude antigen with the caudal fold test.

| Test Results | Caudal fold Test | MPB-70 ELISA | Crude antigen ELISA | |
|---|---|---|---|---|
| True Negative | 49 | 92 | 59 | culture negative |
| False Positive | 50 | 7 | 40 | animals |

TABLE 6

Western blot analysis of *M. bovis* fusion proteins with sera from *M. bovis* infected cattle.

| Number of sera | Molecular weight of cloned antigen | | | |
|---|---|---|---|---|
| tested | 19k | 22k | 65k | 70k |
| 47 | 1* | 36 | 4 | 3 |

*number of sera giving a positive signal
MPB-70 = 22k protein.
The 19, 65 and 70k proteins have previously been cloned and described (Shinnick et al. 1987)

Further features of the present invention will be apparent from the following detailed Examples and the accompanying drawings.

In the drawings:

FIG. 1 shows separation of *M. bovis* antigens on a Mono-P column by chromatofocusing. Freeze dried culture filtrate, approx. 15 mg was dissolved in 0.5 ml of 1:10 Polybuffer PB-74, pH 4.0 and applied onto the column. Fractions were analysed by SDS-PAGE and Western blotting for monoclonal antibody reactivity. Arrowed peaks contain reactive antigen(s). The fractions for each of these peaks were combined.

FIG. 2 shows SDS-PAGE and Western blotting analysis of pooled antigens from the Mono-P column. 30 μl of each pool was loaded.

(a) gel stained with silver stain.

(b) Western transfer of similar gel probed with *M. bovis* specific monoclonal antibody (SB10). Lanes (1) mol wt markers, (2) culture filtrate, (3) pool a, (4) pool b, (5) pool c and (6) pool d.

FIG. 3 shows the sequence of the *M. bovis* AN5 of MPB-70 gene, and its translated protein sequence.

FIG. 4 shows probing of various mycobacterial DNA with a MPB-70 gene probe.

EXAMPLES

Example 1

Isolation and Purification of MPB-70 antigen from *M. bovis* AN5 cultures.

1. Mycobacterial cultures were grown in BAI medium for 2 weeks in 5% $CO_2$ in air at 37° C.
2. The culture medium was collected and centrifuged to remove cells and debris. It was then filtered successively through 0.45 μm and twice through 0.22 μm Millipore membranes.
3. The culture filtrate (CF) was concentrated tenfold by ultrafiltration (Amicon YM-5) or by reverse osmosis against Aquacide II (Calbiochem). The buffer was exchanged for dist. $H_2O$ and the antigens were lyophilized.
4. The lyophilized material was dissolved in a small volume of a tenfold dilution of Polybuffer PB-74 (Pharmacia) which was adjusted to pH 4.0 with imino-diacetic acid (IMDAA). Precipitated antigens were removed by centrifugation and the supernatant was applied onto a chromatofocusing column (Pharmacia Mono-P, 0.5×20 cm, or a 1.5×60 cm column packed with Pharmacia PBE-94 gel) which was equilibrated with 0.025M piperazine adjusted to pH 5.6 with IMDAA. The antigens were eluted with ≅14 column volumes of PB-74 diluted tenfold and adjusted to pH 4.0 with IMDAA. The elution was monitored by absorbance at 280 nm.
5. Fractions containing MPB-70 were pooled and further purified by gel filtration. When minor contaminants were present the preparation was further purified by passing it through a Sepharose Con A column and/or a Superose 12 (Pharmacia) column.

Example 2

Use of Purified MPB-70 antigen in Assays (a) MATERIALS AND METHODS

Antisera and Monoclonal Antibodies. Sera from immunized animals, from naturally or experimentally *M. bovis* infected animals, and from non-infected control animals were used.

Cattle were immunized by repeated subcutaneous injection of 10 mg of killed *M. bovis* (AN5 strain) in 1 ml of saline. Cattle were also infected with live *M. bovis* (AN5) by either intravenous (i.v.) or intratracheal (i.t.) injection of $10^6$ bacteria.

Monoclonal antibodies against irradiated *M. bovis* sonicate, were raised and kindly provided by Agen Biomedical Ltd. They have been characterized and designated SB1-SB10 (Wood et.al., 1988). ELISA. Polystyrene microtitre trays (Nunc Immuno Plate) were coated with 100 μl of 3 μg/ml of *M. bovis* culture filtrate or, 10 μg/ml of purified antigen in phosphate buffered saline (PBS) (pH 7.2) overnight at 4° C. Plates were then washed 4 times in PBS with Tween 20 (PBST), blocked with 0.1% sodium casein, and sera diluted in PSBT were added. Trays were incubated for 90 min at room temperature washed and reincubated with an antibovine antibody conjugated to horseradish peroxidase (HRP:Miles).

After 90 min the trays were washed and incubated with substrate [(2,2'-azino-di(3-ethylbenzthiazoline sulphonate)] (ABTS) for 30 min. Results were read at 405 nm in a Tiretrek Multiskan.

Immunization and skin testing of guinea pigs. Guinea pigs were sensitized with a suspension of killed and dried *M. bovis* strain AN5 in a paraffin oil at a concentration of 0.5 mg/ml. An initial dose of 0.4 ml was given by injecting 0.1 ml subcutaneously at each of four sites. A booster injection of 0.2 ml was given intradermally at two sites 37 days later. Skin testing was conducted 40 days after the second inoculation.

For each antigen two groups of five guinea pigs were used. One group consisted of sensitized animals and the other non-sensitized controls. Each guinea pig was inoculated intradermally with 50 μl of each of three tenfold dilutions of only one antigen. The response to this antigen was assessed at 48 hours by measuring the diameter and area of erythema.

The responses to the purified antigens were compared to an equal weight of bovine tuberculin PPD (Commonwealth Serum Laboratories, Aust.).

Preparation of peripheral blood lymphocytes (PBL). Ten to 20 ml of blood was collected into vacutainers (Becton- Dickinson) containing heparin (20 units/ml) or sodium citrate (3.8%). The blood was then centrifuged at 800 g for 20 min, the buffy coat removed, diluted up to 10 ml with Hanks (GIBCO:Ca$^{++}$, Mg$^{++}$ free) and overlayed onto 10 ml of lymphopaque (BDH: 1.086 g/ml). After centrifuging at 800 g for 25 min the interphase cell layer was collected and washed twice (450 x g; 10 min) with 20 ml Hanks. The cells were finally resuspended in 5 ml RPMI 1640 (GIBCO) and viable counts done using eosin (0.2%) exclusion.

Lymphocyte Proliferation Assay. Isolated lymphocytes were cultured in flat-bottom 96 well trays (Nunc) at $2.5 \times 10^5$ cells/well in RPMI containing 5% foetal calf serum, L-glutamine, 2-Mercaptoethanol and antibiotics. After 48 hour incubation with antigen (25 µl/well) the cultures were pulsed with tritiated thymidine (Amersham; 0.5 µCi/well) and harvested 24 hours later using an automatic cell harvester (Skatron). The amount of tritiated thymidine incorporated was determined using an appropriate scintillant by counting in a liquid $\beta$ scintillation counter. Results were expressed as mean counts per minute (CPM) of triplicate cultures, and the stimulation index calculated as shown below.

$$\text{Stimulation index } (S.I.) = \frac{\text{mean CPM with antigen}}{\text{mean CPM without antigen}}$$

SDS-Polyacrylamide Gel Electrophoresis. Antigens were characterised by their electrophoretic mobility on 15% polyacrylamide gel cast on a Bio-Rad Protean II apparatus. Three centimeters of 4% polyacryalmide stacking gel was used. The buffer system was that of Laemmli (1970) Electrophoresis was carried out at room temperature at 20 mA per gel through the stacking gel and then at 25 mA per gel through the separating gel. In some experiments a Bio-Rad mini gel apparatus was used. The buffers and gel concentrations were as above. Electrophoresis was carried out at 150 volts for approx. 1.5 hours. The gels were stained with Coomassie Brilliant Blue (CBB) and/or with silver stain (Bio-Rad).

Immunoblotting. Antigens from SDS-PAGE, gels were transferred electrophoretically onto nitrocellulose membranes according to the method of Towbin et.al. (1979). The membranes were probed for two hours with antisera or monoclonal antibodies diluted in PBST. They were then incubated with HRP-conjugated sheep anti-bovine, or anti-mouse IgG (Silenus), followed by the HRP substrate (4-chloro-1-naphthol) until the reactive bands were visible.

(b) RESULTS.

Purification of single components containing the specific determinants was achieved by chromatofocusing on a Mono-P column as described in Example 1. FIG. 1 shows a typical elution profile of this step. The arrowed peaks contain most of the antigen that binds to the M. bovis specific monoclonal antibodies but all the peaks eluted after the first arrowed peak (a) contain material that reacts with the monoclonal antibodies. The mol. wt. of the antigens in all the following peaks were 22K. The fractions in each arrowed peak were pooled. FIG. 2(*a*) shows the SDS-PAGE patterns of these pools and FIG. 2(*b*) shows the reaction of the antigens with the monoclonal antibody (SB10), after they were transferred onto nitrocellulose. Western transfers of the purified antigens probed with serum from an *M. bovis* infected animal, also show single reactive bands (result not shown).

The elution pattern varied somewhat for different CF batches showing-considerable variation in their content of the antigen in relation to the total protein (FIG. 2(*a*)). The amounts of the higher mol. wt. species present, which contained the reactive epitopes, also varied. In some cases they were only minimal (FIG. 2(*a*)) and in others quite considerable. The lower the relative amounts of these higher species, the better the recovery of the 22K protein. When the higher species were relatively abundant, small amounts could be recovered in the chromatofocusing purification, often co-purifying with the 22K bands. They were removed if the CF was first passed through a Con A-Sepharose column. This suggests that the larger molecules contain a sugar moiety. The Con A Sepharose step improved the recovery of the 22K protein.

Gel filtration was used to remove additional contaminants when necessary.

Antigens from pools a, b and c were tested in an ELISA system for their suitability for diagnostic use. Crude CF was used as a comparison. A panel of sera of *M. bovis* infected and non-infected animals were tested as well as some sera from animals infected with related mycobacteria and other bacteria.

Sera from *M. bovis* is infected animals that gave high ELISA values with the CF were tested against the purified antigens. In this experiment only antigens 'b' and 'c' were examined, however in earlier experiments it was found that antigen 'a' gave similar ELISA readings to 'b' (result not shown).

MPB-70 was also examined in CMI tests both in vivo and in vitro. The in vivo tests were carried out using the conventional skin test on guinea pigs which were sensitized with *M. bovis* cells. MPB-70 gave a positive reactions although it was not as active as PPD at the lower concentrations tested (Table 2).

MPB-70 was also tested in vitro for its ability to induce proliferation of peripheral blood lymphocytes from *M. bovis* infected cattle. The protein induced similar levels of reactivity in all the *M. bovis* infected animals and showed no activity with lymphocytes from uninfected control animals. The absolute level of reactivity of MPB-70 was less than that seen with *M. bovis* PPD antigen and varied considerably between individual animals.

Example 3

Cloning of *M. bovis* AN5 DNA into λgtll and Detection of Clones Expressing Specific Antigens of *M. bovis*.

(a) MATERIALS AND METHODS

Phase and bacteria. λgtll, *Escherichia coli* Y1089, and *E. coli* Y1090 have been previously described (Young & Davis, 1983), as has the pEX expression vector (Stanley & Luzio, 1984). *M. bovis* AN5 was obtained from the Commonwealth Serum Laboratories, Parkville, Australia. The Commonwealth Serum Laboratories obtained the strain from the Ministry of Agriculture Weybridge Laboratories, England, in 1973. Subsequently, it has been stored in freeze-dried ampoules.

Enzymes. All enzymes were purchased from Promega Biotec. Except where specifically mentioned, all of the DNA techniques used were as described by Maniatis et.al., (1982).

Mabs. Mabs to *M. bovis* were a generous gift from Agen Biomedical Australia Ltd. The properties of MAbs SB1 to SB10 are published elsewhere (Wood et.al., 1988). Isolation of *M. bovis* DNA. *M. bovis* AN5 was grown on BAI medium (Paterson et.al., 1958) for 6 weeks, after which cells were harvested by centrifugation. DNA extraction was essentially by the method of Shoemaker et.al. (1986).

Construction of the *M. bovis* library in λgtll. *M. bovis* DNA was sonicated briefly (~3 secs) at low power, giving DNA fragments ranging in size from 2 kilobase pairs to 200 base pairs (bp), as assessed by agarose gel electrophoresis. DNA methylation, flushing with T4 DNA polymerase, and addition of EcoRI linkers were by the protocol of Young et.al.

(1985). Elimination of excess EcoRI linkers after linker ligation and EcoRI digestion was achieved by using gel filtration (Superose 12 column; Pharmacia), and the eluate was monitored by UV absorption. The DNA was then ethanol precipitated and suspended in the TE buffer, and 0.5 μg was ligated with 1 μg of dephosphorylated EcoRI-digested λgt11 (Promega) overnight at 4° C. Phage packaging was in Stratagene gigapack extracts.

Preparation of affinity-purified antibody to *M. bovis*. An emulsion of approximately $2 \times10^9$ heat-killed mycobacterial cells in Freund incomplete adjuvant was used for hyperimmunization of rabbits. Rabbits received two inoculations, 35 days apart. Blood was taken from the ear of each rabbit 10 days after the second inoculation. Sera were collected, and the titer to *M. bovis* PPD (Commonwealth Serum Laboratories) was determined by enzyme-linked immunosorbent assay. Rabbit sera used in affinity purification gave titers of 1:40,960, as determined by enzyme-linked immunosorbent assay. An *M. bovis* affinity column was prepared by coupling *M. bovis* PPD to Sepharose 4B by the method of March et.al, (1974). The column (20 ml) was equilibrated with 3 volumes of affinity buffer (0.1M Tris, 0.5M NaCl, 0.1% Tween 20), 5 ml of rabbit serum was pumped through, and the column was then washed with 3 volumes of affinity buffer to elute unbound material. Bound substances were then eluted with 2M glycine hydrochloride (pH 2.5) into 2M Tris, and the eluate was monitored by UV absorption. Eluted protein was concentrated by using an Amicon concentrator and washed with phosphate-buffered saline (PBS), and the protein concentration was determined by the method of Bradford (1976).

Screening of the λgtll library. Filters were taken from 85 mm-diameter phage overlay plates prepared as described by Young et.al., (1985). Immediately after removal from the plates, filters were washed for 10 min. in PBST and then blocked in PBS-5% bovine lacto transfer technique optimizer (skim milk) for 1 h. Affinity-purified antibody to *M. bovis* was added to 3.5 μg $ml^{-1}$, and the filters were shaken gently overnight to 4° C. The filters were then sequentially washed for 10 min in PBS, PBST, and PBS, after which swine anti-rabbit horseradish peroxidase conjugate was added tin PBST (Daiko; 1/300) and the filters were incubated with gentle rocking for 2 h. Washing was repeated, and 4-chloro-1-naphthol substrate was added. Colour development was complete after 15 min. The filters were then washed in distilled water and dried.

Plaques corresponding to reactive spots on the filters were picked off and placed in 1.0 ml of SM medium. Purification was by spotting of 5-μl samples from serial dilutions of the original phage suspensions on lawns of *E. coli* Y1090 for further antibody probing, after which single reactive plaques were picked, suspended and streaked on lawns of *E. coli* Y1090.

When Mabs were used for analysis of isolated clones, preparation of filters was identical to the method described. MAbs were substituted for affinity-purified serum (1/2,000 ascites), and anti-mouse alkaline phosphatase conjugate (Promega; 1/5,000) was used for detection. Filters were developed in 5-bromo-4-chloro-3-indolyl-phosphate-Nitro Blue Tetrazolium substrate.

Protein electrophoresis and Western blotting (Immunoblotting). Protein samples were solubilized by heating at 100° C. for 5 min in Tris hydrochloride (pH 6.8) containing 2% sodium dodecyl sulfate, 5% (vol/vol) glycerol, and 0.002% (wt/vol) bromophenol blue. Vertical slab sodium dodecyl sulfate-polyacrylamide gel electrophoresis was carried out essentially as described by Laemmli (1970), in 12% acrylamide gels. Proteins were transferred to nitrocellulose by electro-blotting overnight. Probing with MAbs (1/2,000) was done by the protocol used for phage spots. Probing with cattle sera was done at 1/50 dilution in PBST for 2 h, and the sera were absorbed with pEX-derived protein bound to nitrocellulose for 1 h before use. Bovine antibodies were detected by using a peroxidase-conjugated antibovine immunoglobulin MAb (Australian Monoclonal Developments).

Sequencing. Sequence analysis was done by the primer extension dideoxy termination method of Sanger et.al. (1980) after subcloning in M13tg130 (Amersham Corp.); the products of the sequencing reaction were analysed on 6% polyacrylamide-8 M urea gels.

(b) RESULTS

Construction of a λgtll library of *M. bovis*. *M. bovis* AN5 DNA was extracted, sonicated, and cloned into λgtll. Australian PPD for use in the bovine caudal-fold-skin test is isolated from *M. bovis* AN5, and since PPD is a proven diagnostic reagent, this was the strain chosen for extraction of DNA for cloning. The AN5 library contained $2.5\times10^6$ independent PFU, of which 90% were recombinant as assessed by β-galactosidase inactivation. The sizes of the inserts, as measured by restriction digestion and agarose gel analysis of the library, ranged from 200 to 900 bp.

Probing the *M. bovis* AN5 library with polyclonal sera. Twenty filters representing $5\times10^4$ PFU per filter ($10^6$ PFU overall) were probed with affinity-purified polyclonal anti-*M. bovis* AN5 serum. Between two and eight reactive phage plaques were found on each filter, and these were picked off the plates and further purified. The signal strength of each plaque varied greatly, ranging from barely perceptible dots to conspicuous spots. Not all of the filter spots revealed further reactions on phage purification; of the 88 spots found on the original filters, 32 phage gave consistent signals and passed through primary and secondary purification steps. Very little background due to *E. coli* cross-reactive antibody was found by using the affinity-purified antibodies, in contrast to the situation when unpurified sera from either rabbits or cattle were used. Absorption with lysate either bound to nitrocellulose or added directly to serum was far less effective in reducing background signal than the use of affinity-purified antiserum.

Analysis of recombinant clones with MAbs. Purified phage preparations and lysogens of the λgtll clones reactive with polyclonal antibody were probed with *M. bovis*-*M. tuberculosis*-specific MAbs SB1 to SB10 in phage spot and colony assays to check for the presence of the specific epitopes.

Of the 32 recombinant phage, 5 expressed antigens that were recognised by at least one of the MAbs when phage spots were probed, although as might be expected of antigens derived from a randomly cloned library, not all of these five clones were recognised by all of the MAbs (Table 7). Since MAbs SB1 to SB10 are known to recognise three separate epitopes on the protein antigen MPB70 (Wood et.al., 1988), this is indicative that the recombinant antigens recognised by the MAbs are coded by clones derived from separate ligation events carrying inserts representing different sections of the MPB70 gene.

Of the five λgtll clones recognised by the MAbs, two designated pB3C and C4a, displayed affinity for all of the MAbs in the panel, with the exception of MAb SB9, which did not recognize clone pB3C. Agarose gel analysis showed that clone C4a had an EcoRI fragment insert of ~250 bp. This was the smallest inserted fragment found that carried all of the specific epitopes and was capable of coding for less than half of MPB70 (molecular weight, 22,000). As such it was possible that this clone carried none of the cross-reactive epitopes thought to be present on MPB70 (Harboe & Nagai, 1984) and might prove useful as an antigen in serological diagnosis of BTB.

TABLE 7

Recognition of *M. bovis* clones by SB MAbs*

Reactivity with the following clones:

| MAb | pB2a | pB3c | C4a | X32a | XC2a |
|---|---|---|---|---|---|
| SB1 | − | + | + | − | − |
| SB2 | − | + | + | + | − |
| SB3 | − | + | + | − | − |
| SB4 | − | + | + | − | − |
| SB5 | − | ± | + | − | − |
| SB6 | − | + | + | + | − |
| SB7 | − | + | + | + | + |
| SB8 | − | ± | + | − | − |
| SB9 | − | − | + | − | − |
| SB10 | + | + | + | + | + |

*Reactivity was assessed by probing of phage spots. Drops (5 µl) containing ~10³ phage were spotted on *E. coli* Y1090 lawns, and filters were prepared and probed as described in the text. The symbol ± indicates a weak reaction.

To facilitate serological analysis, the C4a insert was cloned into the high-expression pEX vector (Shoemaker et.al., 1986), and expression was confirmed by immunoblotting of colonies with the SB10 MAb. The pEX vectors express cloned proteins as a cro-β-gal fusion protein, insoluble in most aqueous solutions, which allows for a relatively simple initial purification, eliminating most soluble proteins by washing in 1% Nonidet P-40-1% deoxycholate in PBS. After the washed pEX C4a fusion protein was dissolved in sodium dodecyl sulfate loading buffer, the mixture was run on an acrylamide gel before transfer to nitrocellulose. Sera from both *M. bovis*-infected and healthy cattle were used to probe the Western blots. These blots indicated that antibody reactive to the fusion protein was limited to infected animals. However, not all animals with the disease had a detectable antibody response to the cloned protein. Neither pooled sera from BTB-free herds nor six sera from uninfected cattle in a BTB-infected herd showed reactions with the cloned protein, although it was necessary to absorb out anti-*E. coli* activity in the sera and to use a specific monoclonal antibovine immunoglobulin conjugate to lower cross-reactivity.

Sequence of the MPB-70 gene. Synthetic peptides containing the specific epitopes of MPB70 have diagnostic potential and should be totally free of endogenous cross-reactions. To obtain the DNA sequence of the MPB-70 gene, and consequently the peptide sequence of the MPB-70, a clone of the MPB-70 gene was isolated. The insert from λgt11 clone C4a was used to probe a long-fragment library of *M. bovis* AN5 constructed in the vector EMBL3. After purification of an EMBL3 clone reactive by DNA hybridization with the λgt11 C4a insert, DNA was extracted from the EMBL3 clone and analysed by restriction enzyme digestion and agarose gel electrophoresis. Southern blot analysis, again using the λgt11 insert as a probe, showed the MPB-70 gene to be located on a 1.85 Kbpr PstI restriction fragment. Subcloning of the 1.85 Kbpr PstI fragment into the bacteriophage M13 permitted the elucidation of the sequence of the MPB-70 gene. FIG. 3 shows the DNA sequence and inferred protein sequence of the mature protein MPB-70. This protein is produced intracellularly with a signal sequence that is cleared from the mature molecule.

Patarroyo et.al., (1986,1986a) published two quite different peptide sequences for MPB-70 which were obtained by protein sequencing techniques. The sequence described in FIG. 3 aligns with Pattaroyo's (1985a) up to amino acid 112, with 13 variations. From amino acids 112 to 163 there is no similarity. A similar situation occurs with the sequence of MPB-70 given in Pattaroyo (1986). In this case the similarity with our DNA translated sequence (FIG. 3) ends at amino acid 78, prior to which there are seven variations. Following on from amino acid 80 and discounting a 17 amino acid sequence of Pattaroyo's (1986) which is not present in the DNA translated sequence (FIG. 3) these sequences coincide up to amino acid 130, with eight variations. From amino acid 130 to 153 they are totally different.

Example 4

Diagnosis of *M. bovis* infections in deer.

Sera from *M. bovis* infected deer were tested in an ELISA using the MPB-70 protein as antigen. A pool of sera from non-infected deer was used as a negative control and serum from a known *M. bovis* infected cow was used as a positive control. A commercially available monoclonal antibody to bovine IgG, conjugated to horseradish peroxidase (Bi2, Australian Monoclonal Development, Sydney) was found to also bind cervine antibody and was therefore used as a conjugate in this system.

In this MPB-70 ELISA all six infected deer had antibody levels significantly above that of the control serum (Table 8). Thirty-two individual sera from tuberculosis free deer were also tested in this system and found to be negative.

(a) Method

The ELISA system used to test cervine sera was the same as that used for testing bovines, however two steps in the procedure were altered: (1) the blocking step prior to antibody binding was omitted and (2) a monoclonal anti-bovine IgG conjugate was used instead of a polyclonal conjugate.

TABLE 8

MPB-70 ELISA with *M. bovis*-infected Deer Sera

| Infected Sera | Optical Density |
|---|---|
| 1 | 2.9 |
| 2 | 2.9 |
| 3 | 0.9 |
| 4 | 0.5 |
| 5 | 2.8 |
| 6 | 0.5 |
| Negative control | 0.1 |
| Positive control | 2.9 |

All sera from infected deer were obtained from New Zealand. *M. bovis* infection was confirmed by histology and bacteriological culture of tissues from the animals.

Example 5

Use of *M. bovis* DNA sequence as hybridisation probe.

(a) Method

The mycobacteria listed were cultured in 50 ml of Dubos broth media and harvested by centrifugation. Cell pellets were heat-killed at 70° C. and stored frozen at −20° C. until required. Nucleic acid was extracted from the cells as follows. Each of the cell pellets were resuspended in TE buffer to a total volume of 1 ml. The cell suspensions were sonicated for 5 seconds on ice. Proteinase K was added to give a final concentration of 60 μg/ml and the suspensions were incubated at 65° C. for 1 hour. The samples were extracted once with 1 volume of phenol saturated with TE, then once with Leder phenol (50% phenol, 50% CIA

[chloroform:isoamyl alochol, 24:1]), once with an equal volume of CIA and finally with 1 volume of water saturated ether. The nucleic acid was ethanol precipitated and resuspended in 25 μl of water. Concentration of DNA and RNA in the extracts were measured spectroscopically. Aliquots of approximately 200 ng were applied to Hybond-N membrane using a dot blot apparatus. The DNA was denatured and fixed to Hybond-N as described by the manufacturer. The blot was prehybridised and hybridised in a standard solution, including Plotto and sheared herring sperm DNA. The probe used was the 1.85 kb PstI fragment that contains the gene for MPB-70, labelled with $^{32}P$ using a standard method of oligonucleotide priming. Hybridisation was carried out at 37° C. over night. The blot was washed in 1.0 SSC, 0.1% SDS at 65° C. prior to autoradiography.

(b) Results

Figure 4:
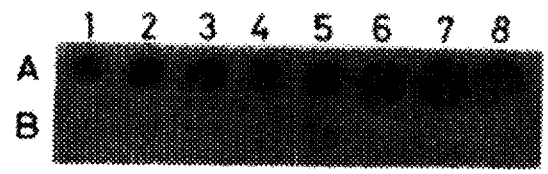

Various DNA preparations of the mycobacteria listed below were probed in dot blots with a radioactive DNA probe of the MPB-70 gene. As can be seen from FIG. 4, all and only M. bovis isolates showed binding of the probe indicating the presence of an homologous MPB-70 gene and surrounding region:

Row (a):
1. *M. bovis* AN5
2. *M. bovis* AN5
3. Field isolate a, Nth.Terr. *M. bovis*
4. Field isolate b, Nth.Terr. *M. bovis*
5. Fetal pig isolate, *M. bovis*
6. Victorian abattoir isolate, *M. bovis*
7. New Zealand possum isolate, *M. bovis*
8. *M. bovis* BCG Row (b):
1. MAIS 2
2. MAIS 2
3. *M. phlei*
4. *M. phlei*
5. *M. Kansasii*
6. *M. Kansasii*
7. MAIS 8
8. MAIS 8

REFERENCES

1. Auer, L. A. (1987), Assessment of an enzyme linked immunosorbent assay for the detection of cattle infected with *Mycobacterium bovis*. *Aust. Vet. J.* 64:172–176.
2. Bradford, M. M. (1976). A rapid and sensitive method for the quantitation of microgram quantities of protein utilizing the principle of protein-dye binding. *Anal. Biochem.* 72:248–254.
3. Daniel, T. M. and Janicki, B. W. (1978). Mycobacterial antigens: a review of their isolation, chemistry, and immunological properties. *Microbiol. Rev.* 42:84–113.
4. Harboe, M., and Nagai, S. (1984). MPB70, a unique antigen of *Mycobacterium bovis* BCG. *Am. Rev. Respir. Dis.* 129:444–452.
5. Harboe, M., Nagai, S., Patarroyo, M. E., Torres, M. L., Ramirez, C. and Cruz, N. (1986). Properties of proteins MPB64, MPB70 and MPB80 of *Mycobacterium bovis* BCG. *Infect. Imm.* 52:293–302.
6. Haslov, K., Anderson, A. D. and Bentzon, M. W., (1987). Biological activity in sensitized guinea pigs of MPB70, a protein specific for some strains of *Mycobacterium bovis* BCG. *Scand. J. Immunol.* 26:445–454.
7. Laemmli, U.K. (1970). Cleavage of structural proteins during the assembly of the head of bacteriophage T4. *Nature* (London) 227:680–685.
8. Maniatis, T., Fritsch, E. F. and Sambrook, J. (1982). Molecular cloning: a laboratory manual. Cold Spring Harbor Laboratory, Cold Spring Harbor, N.Y.
9. March, S. C., Parikh, I. and Custrecasas, P. (1974). A simplified method for cyanogen bromide activation of agarose for affinity chromatography. *Anal. Biochem.* 60:149–152.
10. Miura, K., Nagai, S., Kinomoto, M., Haga, S. and Tokunaga, T. (1983). Comparative studies with various substrains of *Mycobacterium bovis* BCG on the production of an antigenic protein MPB70. *Infect. Immun.* 39:540–545.
11. Nagai, S., Matsumoto, J. and Nagasuga, T. (1981). Specific skin-reactive protein from culture filtrate of *Mycobacterium bovis* BCG. *Infect. Immun.* 31:1152–1160.
12. Patarroyo, M. E., Parra, C., Pinilla, C., delPortillo, P., Lozada, D., Oramas, M., Tores, M., Clavijo, P., Ramirez, C., Fajardo, N., Cruz, N., and Jimenez, C. (1986). Immunogenic synthetic peptides against *Mycobacterium tuberculosis*, 219–229. In F. Brown, R. M. Chanock and R. A. Lerner, (ed), *Vaccines* 86: new approach to imunization. Cold Spring Harbor Laboratory, Cold Spring Harbor, N.Y.
13. Patarroyo, M. E., Parra, C. A., Pinilla, C., delPortillo, P., Torres, M. L., Clavijo, P., Salazar, L. M., & Jimenez, C.. Instituto de Inmunologia, Hospital San Juan de Dios, Universidad Nacional de Colombia, Bogota, Columbia. (1986a)
14. Paterson, A. B., Stuart, P., Leslie, I. W. and Leech, F. B. (1958). The use of tests on sloughterhouse cattle for estimating relative potencies of tuberculins and for the calculation of discrimination tests. *J. Hyg.* 56:1–18.14.
15. Ritacco, V., deKanter, I. N., Barrera, L., Nader, A., Bernardelli, A., Torres, G., Errice, F. and Fliess, E. (1987). Assessment of the sensitivity and specificity of enzyme-linked immunosorbent assay (ELISA) for the detection of mycobacterial antibodies in bovine tuberculosis. *J. Vet. Med. Ser. B.* 34:119–125.
16. Sanger, F., Coulson, A. R., Barrell, B. G., Smith, A. J. H. and Ree, F. 91980). Cloning in single-stranded bacteriophage as an aid to rapid DNA sequencing. *J. Mol. Biol.* 143:161–178.
17. Shinnick, T. M., Krat, C. and Schodow, S. (1987). Isolation and restriction site maps of the genes encoding five *M. tuberculosis* proteins. *Infect. Immun.* 55:1718–1721.
18. Shoemaker, S. A., Fisher, J. H., Jones, Jr., J. D, and Scoggin, C. H. (1986). Restriction fragment analysis of chromsomal DNA defines different strains of *Mycobaterium tuberculosis*. *Am. Rev. Respir. Dis.* 134:210–213.
19. Stanley, K. K. and Luzio, J. P. Construction of a new family of high efficiency bacterial expression vectors: identification of cDNA clones coding for human liver proteins. *EMBO J.* 3:1429–1434.
20. Thoen, C. O., Hall, M. R., Petersburg, T. A., Harrington, Jr., R. and Pietz, D. E. (1983). Application of a modified enzyme-linked immunosorbent assay for detecting mycobacterial antibodies in the sera of cattle from a herd in which *Mycobacterium bovis* infection was diagnosed, P.603–610. In Proceedings of the 87th Annual Meeting of the U.S. Animal Health Association, Las Vegas, Nev.
21. Thorns, C. J. and Morris, J. A. (1983). The immune spectrum of *Mycobacterium bovis* infections in some mammalian species: a review. *Vet. Bull* 53:543–550.
22. Towbin, H., Staehelin, T. and Gordon, J. (1979). Electrophoretic transfer of proteins from polyacrylamide gels to nitrocellulose sheets: procedure and some applications. *Proc. Natl. Acad. Sci. USA.* 76:4350–4354.
23. Wood, P. R., Ripper, J., Radford, A. J., Bundesen, P. G., Rylatt, D. B., Cottis, L. E., John, M. and Plackett, P.

(1988). Production and characterisation of monoclonal antibodies specific for *Mycobacterium bovis*. *J. Gen. Micro.* 134:2599–2604.

24. World Health Organization. (1983). Diagnosis of animal health in the Americas. Scientific publication No.452, Pan American Health Organization, Washington, D.C.

25. Young, R. A., and Davis, R. W., (1983). Yeast RNA polymerase II genes: isolation with antibody probes. *Science* 222:778–782.

26. Young, R. A., Mehra, V., Sweetser, D., Buchanan, T., Clark-Curtiss, J., Davis, R. W. and Bloom, B. R. (1985). Genes for the major protein antigens of the leprosy parasite *Mycobacterium leprae*. *Nature* (London) 316:450–452.

We claim:

1. An isolated DNA molecule containing a DNA sequence which codes for the MPB-70 protein of *M. bovis* having the amino acid sequence of FIG. 3, or for an antigenic polypeptide derived therefrom reactive with affinity-purified antibody to *M. bovis*.

2. A method for preparing protein or polypeptide wherein a transformed host cell or organism is cultivated under suitable conditions and the expressed protein or polypeptide is recovered and purified; said protein or polypeptide being the MPB-70 protein of *M. bovis* having the amino acid sequence of FIG. 3, or an antigenic polypeptide derived therefrom which is reactive with affinity-purified antibody to *M. bovis;* and said transformed host cell or organism contains the DNA as claimed in claim 1.

3. A transformed host cell or organism capable of expressing the MPB-70 protein of *M. bovis*, containing a DNA molecule as claimed in claim 1.

4. MPB-70 protein of *M. bovis* having the amino acid sequence of FIG. 3, or an antigenic polypeptide derived therefrom reactive with affinity-purified antibody to *M. bovis*, produced by expression of a DNA molecule as claimed in claim 1.

5. A method for preparing protein or polypeptide wherein a transformed host cell or organism is cultivated under suitable conditions and the expressed protein or polypeptide is recovered and purified; said protein or polypeptide being the MPB-70 protein produced by expression of DNA which includes the base sequence of FIG. 3; and said transformed host cell or organism contains said DNA of FIG. 3 capable of being expressed to form said protein or polypeptide.

6. The DNA of claim 1 wherein said DNA includes the base sequence of FIG. 3.

7. A recombinant cloning vehicle or vector containing the DNA as claimed in claim 1.

8. A transformed host cell or organism capable of expressing MPB-70 protein of *M. bovis*, containing the DNA as claimed in claim 1.

9. MPB-70 protein produced by expression of the DNA of claim 6.

10. A recombinant cloning vehicle or vector containing a DNA molecule as claimed in claim 1.

11. A method for the detection of *M. bovis* organisms in a sample, which comprises the step of contacting said sample with a DNA probe corresponding to all or a portion of the *M. bovis* DNA sequence coding for the MPB-70 protein of FIG. 3, and detecting hybridisation of said probe to indicate the presence of said organisms in said sample.

12. A test kit for the detection of *M. bovis* organisms in a sample, containing a DNA probe corresponding to all or a portion of the *M. bovis* DNA sequence coding for the MPB-70 protein of FIG. 3.

* * * * *